United States Patent [19]

Tretbar

[11] Patent Number: 4,675,008
[45] Date of Patent: Jun. 23, 1987

[54] T-TUBE

[76] Inventor: Lawrence L. Tretbar, 8901 W. 74th St., Shawnee Mission, Kans. 66204

[21] Appl. No.: 784,230

[22] Filed: Oct. 4, 1985

[51] Int. Cl.$^4$ .......................................... A61M 25/00
[52] U.S. Cl. ......................................... 604/284; 604/8
[58] Field of Search ............... 604/284, 280, 282, 281, 604/264, 8, 9, 52, 49; 128/DIG. 26

[56] References Cited

U.S. PATENT DOCUMENTS

| | | |
|---|---|---|
| 2,624,341 | 1/1953 | Wallace . |
| 2,819,719 | 1/1958 | Utley et al. . |
| 3,392,722 | 7/1968 | Jorgensen . |
| 3,682,180 | 8/1972 | McFarlane ................. 128/DIG. 26 |
| 3,835,862 | 9/1974 | Villari . |
| 3,835,863 | 9/1974 | Goldberg et al. . |
| 3,957,054 | 5/1976 | McFarlane ............................ 604/282 |
| 4,142,528 | 3/1979 | Whelan, Jr. et al. . |
| 4,256,102 | 3/1981 | Monaco .................................. 604/8 |
| 4,257,422 | 3/1981 | Duncan ............................... 604/282 |
| 4,445,897 | 5/1984 | Ekbladh et al. ..................... 604/280 |
| 4,501,263 | 2/1985 | Harbuck . |
| 4,547,187 | 10/1985 | Kelly ................................... 604/284 |

FOREIGN PATENT DOCUMENTS

| | | | |
|---|---|---|---|
| 666090 | 7/1963 | Canada ............................... 604/284 |
| 2144176 | 3/1973 | Fed. Rep. of Germany ...... 604/349 |

Primary Examiner—Stephen C. Pellegrino
Attorney, Agent, or Firm—Litman, Day & McMahon

[57] ABSTRACT

A flexible T-tube for utilization in surgical procedures and the like includes a flexible crossbar comprising two generally planar and intersecting walls joined at an apex and forming a V-shaped channel communicating with the stem near the center of the apex. The stem has an elliptical outer cross-section near the juncture thereof with the crossbar channel and is aligned such that the major axis of the elliptical cross-section of the stem is aligned generally parallel to the longitudinal axis of the crossbar channel. The walls of the crossbar channel are trimmed prior to insertion into a body duct such that the walls fit generally snugly within the duct.

6 Claims, 7 Drawing Figures

ID
T-TUBE

BACKGROUND OF THE DISCLOSURE

The present invention relates to T-tubes for utilization in surgical procedures and the like and, in particular, to a flexible T-tube for implantation in human body ducts, such as the common bile duct, to provide drainage or access following surgical procedures.

T-tubes have been utilized in surgical and other medical procedures for many years. The conventional T-tube has a crossbar with an internal fluid flow directing lumen or channel which is typically positioned in a duct and a stem also with an internal lumen which communicates with the lumen of the crossbar and which is positioned to pass through the duct to drain to a location remote from the duct.

Certain modifications in T-tubes have been developed to produce advantageous effects. For example, Goldberg et al. in their U.S. Pat. No. 3,835,863 disclose a T-tube having slots along the side of the crossbar opposite the juncture thereof with the stem, such that opposite sides of the crossbar intermesh together to form a smaller cross-section and, therefore, less trauma upon withdrawl of the T-tube from the patient. In their U.S. Pat. No. 4,142,528 Whelan et al. disclosed another common modification which often occurs during surgery wherein the surgeon removes a substantial portion of the back wall of the crossbar.

A common use for a flexible T-tube is for drainage of the common bile duct following surgery performed on the gallbladder and/or common bile duct. In particular, the gallbladder is a lined pouch which is connected to the common bile duct by the cystic duct intermediate the liver and duodenum. Normally, bile flows down the common bile duct into the duodenum to assist in the digestion of fatty foods.

Between meals, bile may be stored in the gallbladder. Gallstones which produce both pain and other symptoms may form in the gallbladder and hamper flow of bile in the tract between the gallbladder and the duodenum or between the liver and duodenum. This often requires surgical procedures to remove the gallstones and may also require removal of the gallbladder.

Normally, an incision is made in the common bile duct between the cystic duct and the duodenum in which a T-tube is inserted following the surgery. The incision in the common bile duct is sewn together on opposite sides of the stem of the T-tube so that only the stem protrudes therefrom. The stem is passed through the abdominal wall of the patient and the T-tube is left in place normally in the range of from 7 to 21 days following surgery. During this period of time, the T-tube allows excess bile to drain from the common bile duct. Normally, after approximately this amount of time, the liver modifies its production of bile to adjust for the gallbladder no longer being present to provide storage. Sometimes the T-tube is utilized to also flush the common bile duct or for other purposes while still inserted therein. After serving its useful purpose, the T-tube is pulled by the distal end of the stem such that opposite sides of the crossbar collapse together and it is then pulled from the body in this manner.

Unfortunately, trauma occurs at the opening for the stem through the common bile duct as the crossbar is pulled through. Attempts have been made to reduce this trauma through various modifications to the T-tube, such as are shown in the above mentioned Goldberg et al. patent. Applicant has found that the trauma can be reduced by making the cross-section of the stem, where is passes through the wall of the common bile duct, elliptical in shape, especially where the largest or major axis of the elliptical cross-section is aligned parallel to the longitudinal axis of the lumen of the common bile duct. This elliptical cross-section produces numerous advantages.

In particular, as compared to circular stems, the elliptical cross-section allows reduction in the width of the stem along the minor axis of the elliptical cross-section as the major axis is widened while still allowing for passage of approximately the same volume through a central lumen thereof. Alternatively, the width of the lumen along the minor axis may be the same as the diameter of a circular stem, yet the internal flow capacity or working space can be increased as the major axis is lengthened.

As wounds or incisions along the common bile duct heal from side to side rather than from the end to the middle, a wound left after removal of an elliptical tube, although relatively longer, has a healing time which is less than the healing time associated with removal of a circular stem capable of containing the same flow and there is less chance of excessive scar formation which could lead to stricture or narrowing of the common bile duct after healing.

Secondly, during suturing of the incision following implantation of the T-tube, it is necessary to suture tightly around the stem to form a liquid seal. For a T-tube suitable for handling a given flow volume, the round tubes produce greater stretching of tissue about the stem than do elliptical tubes as described for the present invention. The greater tension makes suturing more difficult around the circular tubes than around the elliptical tubes as described herein.

Thirdly, under certain circumstances, gallstones may be retained within the common bile duct following surgery. There are techniques for removing these stones without subsequent invasive surgery by introduction of instrumentation through the T-tube. A T-tube of the present invention having a minor axis width equal to that of a circular T-tube leaves a wound after removal which heals approximately as fast as the circular T-tube (as discussed above), but presents a much larger internal working circumference within the tube for insertion of tools making such procedures surgically easier and less traumatic to the surrounding tissue.

Finally, when the T-tube is removed, there is always an associated trauma. Again, in comparing an elliptical T-tube according to the present invention having a minor axis with approximately equal width to a conventional circular T-tube, upon removal, the elliptical tube presents a larger cross-sectional area for passage of the crossbar therethrough as compared with the circular T-tube, yet healing time of the wounds will be approximatley the same.

T-tubes, especially T-tubes for utilization in the common bile duct, are available in many different sizes as the common bile duct normally varies from 0.5 to 1.0 centimeters and, in certain conditions, dilates to 2.5 centimeters or more. Normally, a surgeon selects the outer diameter of the T-tube to generally match the inner diameter of the common bile duct. This means that many different tubular sizes must be available to the surgeon. In addition, in accordance with common procedure, the surgeon will often remove the back side of the T-tube, that is, the side opposite from the side of the tube which abuts against the stitches. Removal of the back side of the tube can be seen in such references as the above discussed Whelan et al. patent. Removal of the back side of the tube could be utilized to adjust the tube to various duct sizes, except that the remaining portion of the tube will retain substantially the same radius as the original tube and, therefore, it will never fit properly within a duct having a different radius.

Therefore, applicant has designed a crossbar formed of two generally planar walls joined in a V-shape which can be trimmed by a surgeon at the time of insertion to conform to the walls of a particular duct into which the surgeon is inserting the tube. In this manner, the surgeon not only can modify a single standard tube to fit a particular need, such as the diameter of virtually any common bile duct; but also the edges of the walls may be sized to abut against the sides of the duct so as to form a snug implantation. Thus, provided that the wall panels are of sufficient initial width, one size of T-tube according to the present invention may be modified to fit virtually all common bile ducts or used for other similar medical procedures requiring a T-tube type drain, including procedures on the kidney and/or ureter and in hysterectomies.

OBJECTS OF THE INVENTION

Therefore, the objects of the present invention are: to provide a T-tube having a stem of elliptical cross-section and providing ease of access and reduced trauma as compared to a T-tube having a diameter generally equal to the minor access of the elliptical cross-section; to provide such a T-tube leaving a relatively fast healing wound after removal thereof; to provide such a T-tube available in a single size which is readily modifiable to fit virtually any common bile duct; to provide such a T-tube which is modifiable to fit snugly within the common bile duct; to provide such a T-tube which has a stem which is relatively easy to suture about to provide a liquid seal; to provide such a T-tube which is relatively easy to manufacture, relatively easy to utilize during surgery and which is especially adapted for the intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
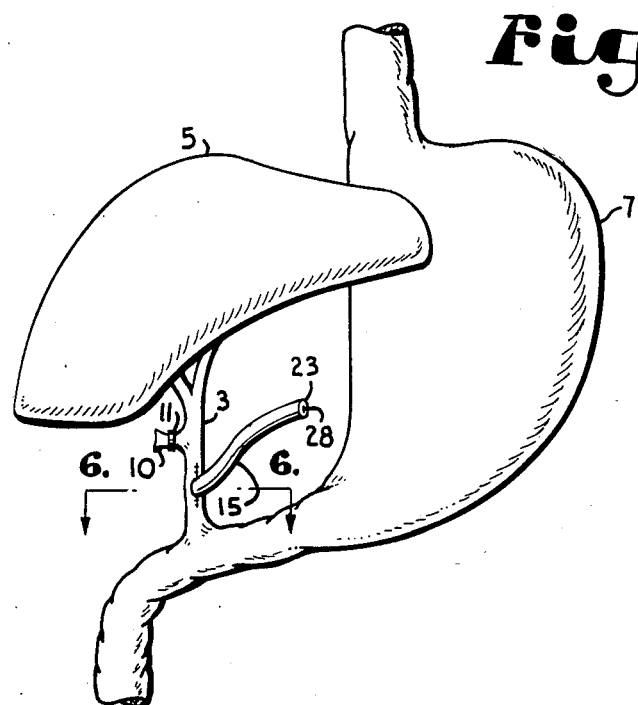
FIG. 1 is a fragmentary front elevational view of internal organs of a human showing approximate placement of the liver, common bile duct and duodenum following a cholecystectomy, showing a T-tube according to the present invention partially positioned in and extending from the common bile duct.
Figure 5:
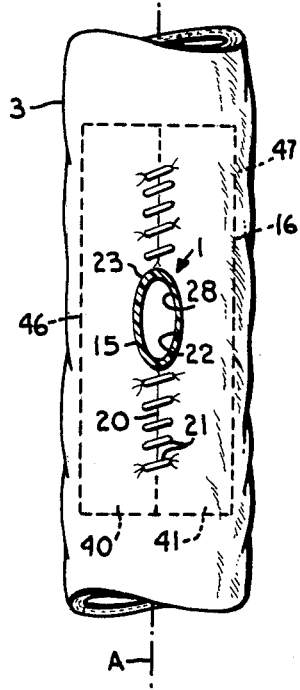
FIG. 5 is a fragmentary and enlarged side elevational view of the common bile duct with the T-tube implanted therein.

A T-tube in accordance with the present invention is generally designated by the reference numeral 1. The T-tube 1 is shown in FIGS. 1 and 5 positioned in a common bile duct 3. The bile duct 3, as seen in FIG. 1, interconnects internal organs of the body including the liver 5 with the duodenum 6 at at location spaced from the stomach 7. A cholecystectomy has been performed on the particular body illustrated in FIG. 1, such that the gallbladder has been removed from the body and a cystic duct 10 which had interconnected the gallbladder with the common bile duct 3 has been severed and closed by clamp 11 to prevent fluid from flowing from the common bile duct 3 through the cystic duct 10.

Figure 6:
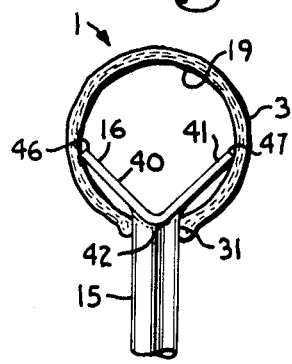
FIG. 6 is a enlarged and fragmentary cross-sectional view of the common bile duct and T-tube, taken along line 6—6 of FIG. 5.

The T-tube 1 comprises a stem 15 and a crossbar 16 joined medially with the stem 15 so as to form a T-shaped configuration, although it is noted that a Y-shape or other semi-T-shape would be functional according to the invention and is included in the term T-tube. As is seen in FIG. 5 and 6, the common bile duct 3 includes an internal lumen 19 in which the T-tube crossbar 16 is surgically positioned. The lumen 19 has a longitudinal axis, designated by the latter A, as seen in FIG. 5. The crossbar 16 is positioned in the common bile duct 3 through a surgical incision or opening 20 which, after implantation of the crossbar 16, is partially closed by closure means, such as stitches 21. During initial implantation of the crossbar 16 in the common bile duct 3, an aperture 22 is left in the common bile duct 3 through which the T-tube stem 15 passes.

Figure 2:
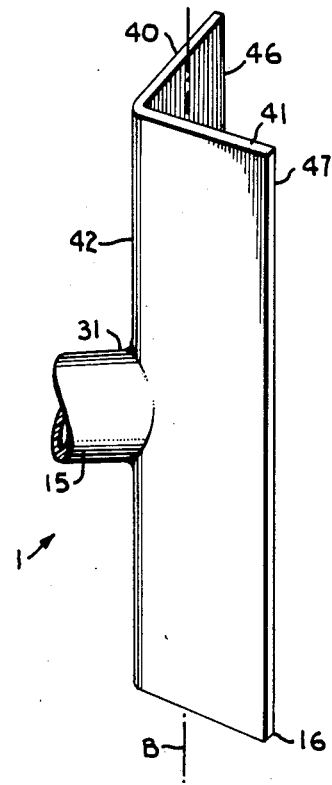
FIG. 2 is a fragmentary and enlarged perspective view of the T-tube showing a crossbar and a portion of a stem thereof.

A distal end 20 of the T-tube stem 15 is normally positioned so as to extend through the abdominal wall of the patient (not shown) to drain fluid from the common bile duct 3 to an exterior location. The surgical opening 20 is preferably tightly closed by the stitches 21 so as to prevent leakage of fluid between the stem 15 and the tissue of the surgical opening 20. The crossbar 16 has a longitudinal axis generally designated by the letter B in FIG. 2. The axes A and B are normally parallel and may be coaxial when the crossbar 16 is operatively positioned within the duct 3.

Figure 3:
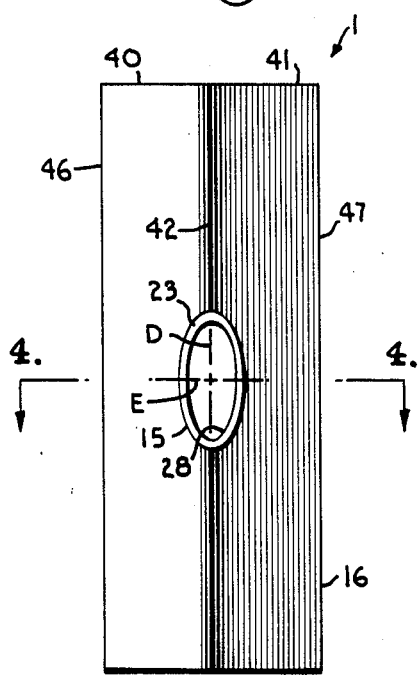
FIG. 3 is an enlarged top plan view of the T-tube.
Figure 4:
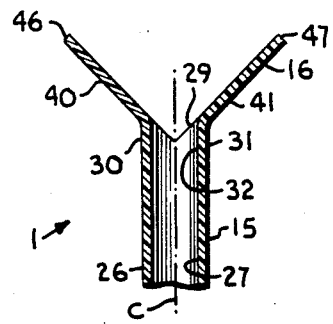
FIG. 4 is an enlarged cross-sectional view of the T-tube, taken along line 4—4 of FIG. 3.

The T-tube stem 15 comprises an elongate flexible shaft 26 having an internal lumen 27. The lumen 27 has an external opening aperture 28 at the distal end 23 thereof and a second aperture 29 at an opposite end and flow communicating with the crossbar 16. The lumen 27 has a longitudinal axis generally designated by the letter C. At the juncture of the crossbar 16 with the stem 15 and near the location 32 whereat the surgical opening aperture 22 engages the stem 15, the external circumference 31 of the stem 15 at and adjacent to the location 30 is ovate or elliptical in shape as is the internal circumference 32 of the cross-section at the same location 30. Although a circle is sometimes considered a special oval or ellipse, as used herein the terms elliptical and oval are understood to mean a closed plane curve generated by a point moving in such a way that the sums of the distances from two fixed points (foci) is a constant and that the curve has a major axis which is longer than a minor axis perpendicular to the major axis, excluding circles. The major axes of both of the curves associated with the internal circumference 32 and the external circumference 31 near the juncture of the stem 15 with the crossbar 16 are aligned to be parallel to a longitudinal axis B of the crossbar. In particular, as seen in FIG. 3, the curve formed by the stem external circumference 32 has a major axis generally designated by the letter D and a minor axis generally designated by the letter E. Preferably, the major axis D is at least twice as wide as the minor axis E.

The crossbar 16 comprises two generally planar yet flexible wall panels 40 and 41 joined at an apex 42 so as to form a conduit, passageway or channel 43 therebetween. The illustrated channel is V-shaped and the walls 40 and 41 are preferably angled approximately 90° with respect to each other. Each wall panel 40 and 41 has an outer edge 46 and 47 respectively. The stem 15 joins with a medial portion of the crossbar 16 approximately centrally along the apex 42. The stem lumen opening 29 flow communicates with the crossbar channel 43.

Figure 7:
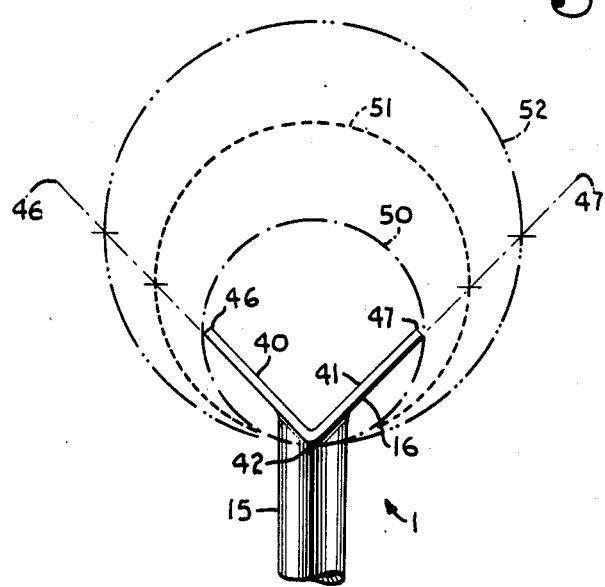
FIG. 7 is a fragmentary and enlarged side elevational view of the T-tube illustrating removal of portions of planar walls of the crossmember to fit various common bile ducts having different internal cross-sectional diameters.

Prior to insertion of the T-tube crossbar 16 into the common bile duct 3, the wall panels 40 and 41 are preferably trimmed to snugly fit within a common bile duct lumen 19. In particular, as seen in FIG. 7, the crossbar panels 40 and 41 are trimmed along the length of the respective panel parallel to the longitudinal axis B of the crossbar 16 and parallel to the respective edges 46 and 47 so as to fit the internal diameter of various sized ducts as represented by the circles 50, 51 and 52. The dash lines in FIG. 7 extending outward from the panels 40 and 41 represent that portion of the panel removed so that the illustrated crossbar 16 will fit a particular duct having a diameter represented by the circle 50.

In use, a surgeon makes an incision represented by the surgical opening 20 in a common bile duct 3. A T-tube 1 is selected which has wall panels 40 and 41 which are wider than necessary to snugly fit within the common bile duct 3. The wall panels 40 and 41 are then trimmed by cutting parallel to the respective edges 46 and 47 thereof such that the remaining crossbar 16 will fit fairly snugly within the common bile duct 3, such as is shown in FIG. 6.

The crossbar 16 is then inserted into the surgical opening 20 so as to be surrounded by the duct 3 after having opposite ends trimmed if necessary to fit the particular opening 20. A back and forth maneuver may be necessary to insert the crossbar 16 as it will usually be longer than the length of the surgical opening 20. The stem 15 is allowed to protrude from the common bile duct 3.

The surgical opening 20 is then partially closed by stitches 21 so as to fit snugly and sealably about the stem 15. The stem distal end 23 is normally positioned exterior of the abdominal wall of the patient to allow draining of excess bile from the common bile duct 3 to a location exterior the body. After the T-tube 1 has served its useful purpose within the common bile duct 3, the stem distal end 23 is pulled. At this time, the opposite ends of the crossbar 16 fold against each other and the crossbar 16 is urged to pass through the surgical opening aperture 22 and drawn from the body. Thereafter, opposite edges of the aperture 22 come together and eventually heal to form a seal against fluid passing through the aperture 22.

It is to be understood that while certain forms of the present invention have been illustrated and described herein, it is not to be limited to the specific forms or arrangement of parts described and shown.

What is claimed and desired to be secured by Letters Patent is as follows:

1. A T-tube for use in an internal human duct having an internal wall; said T-tube comprising:
   (a) an elongate crossbar having a channel passing longitudinally therethrough;
   (b) said crossbar comprising a pair of flexible and generally planar panels joined at an apex to form a V-shaped configuration and forming said channel therebetween; each of said panels having outer ends opposite said apex; said panels being generally larger than usable for a duct prior to use and of such construction to allow trimming to a smaller width prior to placement in said duct, such that said panel outer ends and said apex fit snugly against opposite sides of the duct wall of said duct such that said crossbar is held in a desired position within said duct; and
   (c) a stem having an internal lumen; said stem joined to said crossbar such that said lumen flow communicates with said channel.

2. The T-tube according to claim 1 wherein:
   (a) said T-tube is for use in a common bile duct;
   (b) said panels are originally substantially wider than a normal human common bile duct; and
   (c) said panels are trimmable generally parallel to said apex such that a surgeon can trim said panels to modify said crossbar so that said modified crossbar fits within a particular common bile duct.

3. The T-tube acording to claim 1 wherein:
   (a) said panels are angled at 90° relative to each other.

4. A process for inserting a T-tube in a common bile duct including the steps of:
   (a) providing a T-tube comprising:
      (1) an elongate crossbar having a channel passing longitudinally therethrough;
      (2) said crossbar comprising a pair of flexible and generally planar panels joined at an apex to form a V-shaped configuration and forming said channel therebetween; and
      (3) a stem having an internal lumen; said stem joined to said crossbar such that said lumen flow communicates with said channel;
   (b) forming a surgical incision in said bile duct;
   (c) trimming said panels generally parallel to said apex such that said crossbar will fit snugly into said bile duct after placement therein;
   (d) inserting said crossbar into said bile duct through said incision such that said stem passes through said incision and said crossbar panels are wedged at the apex and at ends of the panels opposite the apex against said bile duct; and (e) utilizing closure means to close said opening and to provide a substantial fluid seal about said stem.

5. The T-tube according to claim 1 wherein:
   (a) said crossbar has a longitudinal axis associated therewith; and
   (b) said stem has an elliptical external cross-section near said crossbar with a major elliptical axis aligned parallel to said crossbar axis.

6. A process for inserting a T-tube in a common bile duct including the steps of:
   (a) providing a T-tube comprising:
      (1) an elongate crossbar having a channel passing longitudinally therethrough;
      (2) said crossbar comprising a pair of flexible and generally planar panels originally substantially wider than said duct and being joined at an apex to form a V-shaped configuration defining said channel therebetween;
      (3) a stem having an internal lumen; said stem joined to said crossbar such that said lumen flow communicates with said channel;
      (4) said crossbar has a longitudinal axis associated therewith; and
      (5) said stem has an elliptical external cross-section near said crossbar with a major elliptical axis aligned parallel to said crossbar axis;
   (b) forming a surgical incision in said bile duct;
   (c) trimming said panels generally parallel to said apex so as to form panel ends opposite said apex and such that said crossbar will fit snugly into said bile duct;
   (d) inserting said crossbar into said bile duct through said surgical incision such that said stem passes through said incision and said panel ends and said apex are snugly wedged against an interior wall of said duct; and
   (e) utilizing closure means to close said opening and to provide a substantial fluid seal about said stem.

* * * * *